(12) United States Patent
Groβ et al.

(10) Patent No.: US 7,938,579 B2
(45) Date of Patent: May 10, 2011

(54) C-ARM MOUNTED ON A ROBOTIC ARM

(75) Inventors: Stefan Groβ, Trabitz (DE); Dieter Heinl, Erbendorf (DE)

(73) Assignee: Siemens Aktiengesellschaft, Munich (DE)

( * ) Notice: Subject to any disclaimer, the term of this patent is extended or adjusted under 35 U.S.C. 154(b) by 39 days.

(21) Appl. No.: 12/349,696

(22) Filed: Jan. 7, 2009

(65) Prior Publication Data

US 2009/0180592 A1    Jul. 16, 2009

(30) Foreign Application Priority Data

Jan. 10, 2008   (DE) .................. 10 2008 003 816

(51) Int. Cl.
    *H05G 1/02*   (2006.01)
(52) U.S. Cl. ........................................ 378/197
(58) Field of Classification Search .......... 378/189, 378/190, 193, 194, 195, 196, 197, 199, 200
    See application file for complete search history.

(56) References Cited

U.S. PATENT DOCUMENTS

| | | | | |
|---|---|---|---|---|
| 4,716,581 A * | 12/1987 | Barud | ............ | 378/198 |
| 4,856,036 A * | 8/1989 | Malcolm et al. | ............ | 378/116 |
| 5,048,069 A * | 9/1991 | Siczek | ............ | 378/197 |
| 5,050,204 A * | 9/1991 | Siczek et al. | ............ | 378/197 |
| 5,426,683 A * | 6/1995 | O'Farrell et al. | ............ | 378/197 |
| 5,436,461 A * | 7/1995 | Saffer et al. | ............ | 250/522.1 |
| 5,761,269 A * | 6/1998 | Sugihara et al. | ............ | 378/199 |
| 6,314,157 B1 * | 11/2001 | Tachizaki | ............ | 378/4 |
| 6,435,715 B1 | 8/2002 | Betz et al. | | |
| 6,789,941 B1 * | 9/2004 | Grady | ............ | 378/197 |
| 6,869,217 B2 | 3/2005 | Rasche et al. | | |
| 7,052,421 B2 * | 5/2006 | Simmons | ............ | 474/101 |
| 7,108,421 B2 * | 9/2006 | Gregerson et al. | ............ | 378/197 |
| 7,591,589 B2 * | 9/2009 | Grebner et al. | ............ | 378/197 |

FOREIGN PATENT DOCUMENTS

DE    102008003088 A1    7/2009

OTHER PUBLICATIONS

German Office Action dated Jan. 28, 2010 for DE 10 2008 003 816.4 with English translation.

* cited by examiner

*Primary Examiner* — Allen C. Ho
(74) *Attorney, Agent, or Firm* — Lempia Summerfield Katz LLC

(57) ABSTRACT

An x-ray device is provided. The x-ray device includes a C-arm that may be rotatably mounted on a robotic arm. A radiation source and a radiation detector may be arranged on the C-arm. The interior of the C-arm, which is hollow at least in sections, is accessible from at least one access side to allow at least a part of the electronic components used to operate the radiation source and the radiation detector to be integrated in the interior of the arm.

14 Claims, 2 Drawing Sheets

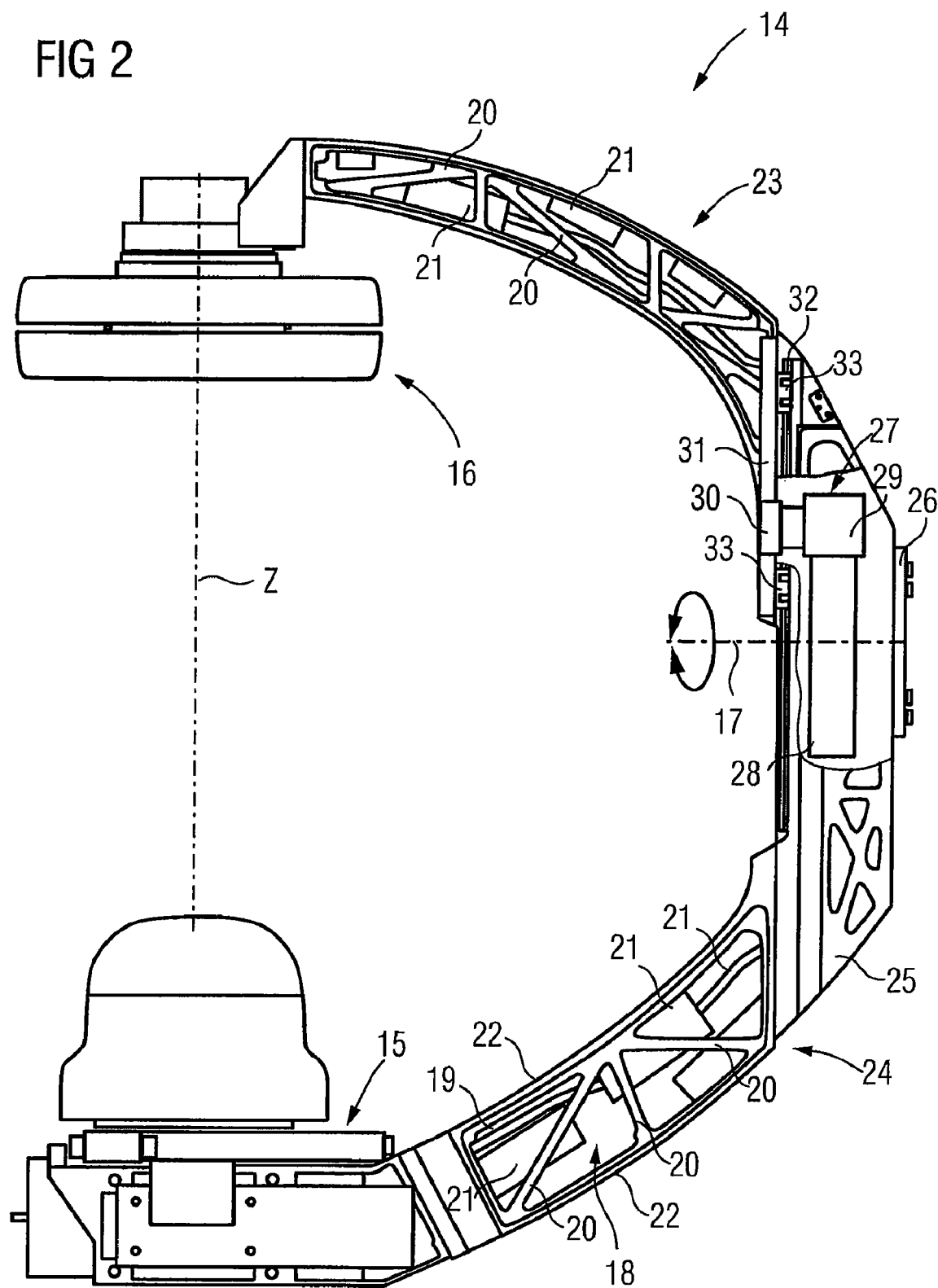

C-ARM MOUNTED ON A ROBOTIC ARM

This patent document claims the benefit of DE 10 2008 003 816.4, filed Jan. 10, 2008, which is hereby incorporated by reference.

BACKGROUND

The present embodiments relate to an x-ray device including a C-arm rotatably mounted on a robotic arm.

X-ray devices include a C-arm that is rotatably arranged on an upright stand on the floor by a swivel guide about a conventionally horizontal axis. In the swivel guide, the C-arm is rotatable about an isocenter along the curved swivel guide. A light C-arm is used in order to achieve as effective a dynamic as possible, especially when the C-arm is moved along the swivel guide at considerable speed. For example, an angiography x-ray device may include a C-arm that is moved along the swivel guide at considerable speed. As a result, C-arms made of extruded profiles that have an essentially rectangular hollow profile cross-section are normally used.

The C-arm may be arranged on a robotic arm. Instead of a floor stand with the swivel guide, which are needed for the necessary degrees of movement, the C-arm may be arranged on an industrial robot with a robotic arm and a corresponding control device. The degrees of freedom are ensured by the six movement axes of the robot, in conjunction with a rotating support of the C-arm on the robotic arm. The C-arm is supported in such cases to allow direct rotation on the robotic arm. The electronic components used to operate the radiation source and radiation detector are arranged externally to the robotic arm and/or moved along with the robotic arm. Unlike with the embodiment with a floor stand having a swivel guide, where these electronic components are integrated on the stand side, a corresponding receiving space is not provided on the robotic arm. This results in correspondingly complex constructions.

SUMMARY AND DESCRIPTION

The present embodiments may obviate one or more of the problems or drawbacks inherent in the related art. For example, in one embodiment, an x-ray device includes a light C-arm, which can be used in conjunction with an industrial robot to move the arm.

In one embodiment, an x-ray device includes a C-arm rotatably mounted on a robotic arm. A radiation source and a radiation detector are arranged on the C-arm. The C-arm is hollow at least in sections and is accessible from at least one access side in order to enable integration in the interior of the C-arm of at least one part of the electronic components used to operate the radiation source and the radiation detector.

The x-ray device may include a hollow C-arm that is open from at least one access side. Because the arm is open, at least in sections, on one side or multiple sides, the overall weight of the C-arm is reduced. The C-arm being configured in accordance with the required rigidity and oscillation criteria etc. This criteria can however be maintained and/or achieved despite the open construction. When using the C-arm in conjunction with an industrial robot and/or robotic arm, at least one part or almost all electronic components, which are used to operate the radiation source and radiation detector, may be integrated into the interior of the C-arm. Unlike hollow C-arms with sides that are completely enclosed, the electronic components of the C-arm, which usually involve components or cables with relatively small dimensions, may be positioned in the interior of the arm. The electronic components do not need to be arranged separately and may be connected to the operating components on the floor by, for example, cable or control line connections and are instead moved using the C-arm. The electronic components are relatively light components, as result of their high integration density. In other words, the weight of all the electronic components to be integrated is not too great. As a result, there is only a relatively minimal weight increase in the C-arm so that the requirements still placed on high dynamics can be achieved despite integration of the electronic components.

The C-arm with the open structure may be used with x-ray devices with a stand on the floor, in which x-ray device the electronic components are then not integrated in the C-arm, as well as robotic x-ray devices, in which at least a part or all electronic components may be integrated in the interior of the C-arm.

The C-arm may be hollow and accessible from the side over its entire length so that sufficient receiving space, in which the electronic components can be arranged, is provided.

The interior of the C-arm may be accessible from access sides, which are arranged opposite to one another. For example, the access sides may be the two side surfaces in the case of a rectangular arm profile, as viewed from the cross-section. The relevant positions on both sides may be reached for assembly or maintenance purposes, thereby facilitating operation. As a result, assembly and accessibility is simple.

The C-arm may be a framework on one access side. For example, struts may be arranged in the form of a framework on one access side. The framework may be applied to both sides in the case of an arm structure, which is open on both sides. The framework construction may be realized on both sides, which may include the same configuration. The C-arm may be a cast part. As a result, the C-arm may be easily manufactured. The embodiment of the framework structure and/or the arrangement of the struts is selected on the one hand in respect of weight optimization, in order to save as much material as possible. The strut arrangement is designed in order to achieve the desired mechanical properties. Material may be saved primarily in the region of low mechanical stresses and/or loads, whereas in regions of a higher mechanical load, corresponding supports are provided in a suitable angular arrangement in respect of each other and/or other arm sections. The design of the structure conforms with the given geometric and mechanical specifications.

In an alternative embodiment, the interior of the C-arm may be subdivided into compartments by separating walls. Such a structure can also be easily realized with a cast part. The compartment, which is accessible from one side, for example, allows the integration of a plurality of electronic components. At least sections of the intermediate walls may be opened to allow connecting or supply lines to be laid through them. The access side may be completely open since the stability is realized by the embodied dividing walls in conjunction with the other three closed side walls.

The, or each, access side may be closed off with a detachable cladding. The detachable cladding may be easily and rapidly removed for assembly or maintenance purposes.

In one embodiment, the C-arm may include two separate arm sections, which are connected to one another to form the curved arm. When installed or assembled, the radiation source is arranged on one arm section and the radiation detector is arranged on the other arm section.

In one embodiment, a lifting device may be provided. The lifting device may move the radiation detector along the axis of the central beam, such as the axis which connects the radiation source directly to the radiation detector. The film focus distance between the radiation source and radiation detector may be varied. With known devices, the lifting device is positioned directly at the end of the arm on the radiation detector itself, which is not always optimal for weight reasons and in respect of the position of the centre of gravity of the arm. The lifting device also protrudes relatively far, viewed radially, thereby restricting the freedom of movement. With the use of a hollow arm accessible from the side, one expedient development provides for the arm sections to be able to be moved relative to one another by a lifting device which is arranged in the interior of the arm. The open arm allows the lifting device to be integrated into the C-arm. The C-arm may be disposed in the region adjacent to the rotational axis bearing of the C-arm, for example, on the robotic arm, so that the center of gravity can be optimized. The C-arm may lay as close as possible to the axis of rotation, which provides even better movement dynamics. The weight at the end of the arm supporting the radiation detector may not be determined to a significant extent by the lifting device, but instead only by the radiation source located there, since the lifting device is arranged in the interior of the arm on the rotating connection thereof on the robotic arm, for example. The C-arm does not protrude sideways in the region of the radiation detector, instead its form is essentially determined by the geometry of the arm.

The C-arm may be rotatably mounted by one arm section, while the other arm section is guided into or onto the one arm section. No additional complex positioning of fastening mechanisms are used, instead the one C-arm section, which is fixed in respect of the lifting movement, and in respect of which the other C-arm is moved by the lifting device is used to fasten directly to the robotic arm. Corresponding mounting options are provided and/or arranged on the arm section. The other arm section is guided on or in this first arm section so as to allow linear movement, for example, the other arm section may be moved linearly relative to this section by the lifting device so that it produces a linear movement of the radiation source relative to the radiation detector. For linear guidance, guide rails are expediently provided, for example, on the fixed arm section, upon which guide rails, corresponding guiding sections of the other arm section run in each instance.

The lifting device may include a driving motor and a lifting mechanism that can be actuated by the driving motor. A speed increase or decrease device may be arranged downstream of the driving motor, depending on how the driving motor and/or the lifting mechanism are designed.

The lifting mechanism can include a stationary toothed wheel, which can be powered by the driving motor and/or a transmission arranged downstream thereof and a gear rack arranged on the arm section to be moved, with which the toothed wheel mates. Alternatively, the lifting mechanism may include a stationary threaded spindle which can be driven by the driving motor. At least one threaded nut connected to the moving arm section may run on the threaded spindle. This list of different mechanical designs is not definitive, any mechanical designs which are of a compact design, in order to allow their integration into the arm, and which allow an adequate lift.

Alternatively, the lifting device may be an electrical, hydraulic or pneumatic actuating cylinder, which is coupled to the two arm sections.

BRIEF DESCRIPTION OF THE DRAWINGS

FIG. 2 shows partial sections of one embodiment of the C-arm.

DETAILED DESCRIPTION

Figure 1:
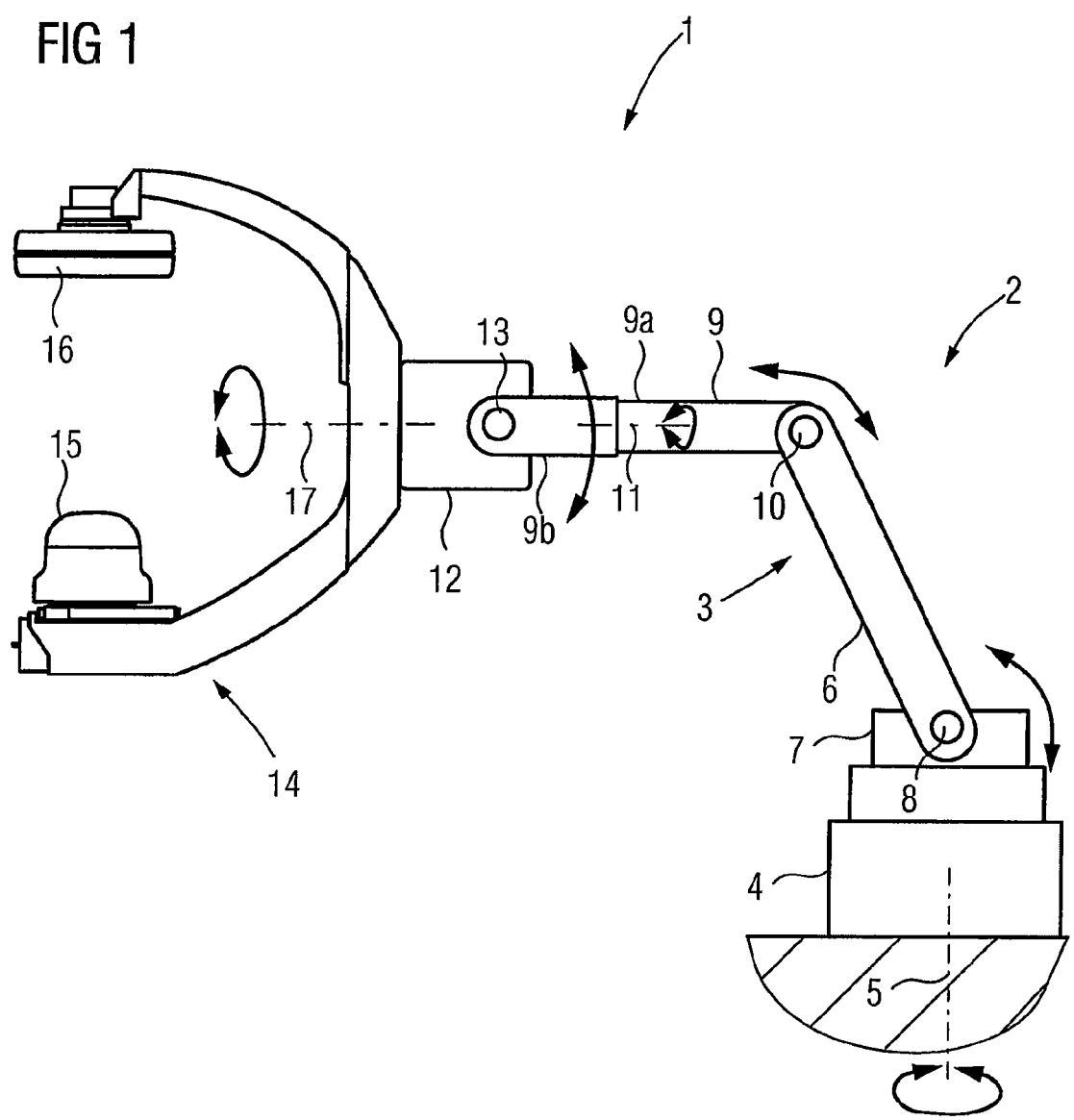
FIG. 1 shows one embodiment of an x-ray device including a C-arm arranged on an industrial robot.

FIG. 1 shows an x-ray device 1 including an industrial robot 2, with a robotic arm 3, which is accommodated on a base 4, arranged on the floor. The robotic arm 3 is rotatable overall on the base about a vertical axis 5. The robotic arm 3 is accommodated on the base 4 by a first robotic arm 6 on a base part 7. The first robotic arm 6 can be rotated about the vertical axis, on which base part 7 it can also be pivoted about a horizontal axis 8. A second robotic arm 9 is positioned on the first robotic arm 6. The robotic arm 9 may be pivotable thereupon about a second horizontal axis 10. The second robotic arm 9 includes the first arm section 9a, which is arranged on the first robotic arm 6, as well as a second arm section 9b, which for its part can be rotated about a further axis 11 relative to the arm section 9a. A C-arm mount 12, which can be rotated about the axis 13, may be positioned on the arm section 9b. The C-arm 14, upon which a radiation source 15 and a radiation detector 16 are arranged, is for its part rotatable on the C-arm mount 12 about a further axis of rotation 17. A 6-axes system, which allows a free movement of the C-arm 14 in space, is provided.

The C-arm 14 is shown in detail in FIG. 2. The C-arm 14 includes an open structure and a hollow interior. Two opposite sides (only the one side is naturally visible in the side view in FIG. 2) are open. As a result, corresponding access sides 18, by way of which access into the interior of the arm 19 is provided, are realized. The two opposing access sides have a framework structure and/or struts arranged in a framework fashion, the dimensioning and arrangement of which is selected such that it allows the best possible rigidity with as little use of material as possible. These two access sides 18, which are usually closed off with appropriate cladding, now allow electronic components 21, of which several are shown by way of example here, to be able to be integrated in the interior of the C-arm 14. These electronic components 21 are used to operate the radiation source 15 and radiation detector 16. These electronic components can be any components or also cables. The electronic components 21 are fastened to the supports 20 or to the remaining side walls 22 of the C-arm by suitable fastening means.

The C-arm 14 includes two arm sections 23, 24, which may be metal cast parts to enable the framework structure to be embodied in a simple fashion. Arm section 24 has a fastening section 25, by way of which it can be arranged with a suitable fastening flange 26 on the C-arm mount 12 of the robotic arm 3. This fastening section 25 can be an integral part of the arm section 24, it can however also be connected to the second arm part which comprises the open access side 18 as a separate cast part, in order then to form the whole first arm section 24.

The arm section 23 can be linearly displaced by a lifting device 27, which is integrated in the interior of the C-arm, relative to the arm section 24 arranged in a fixed fashion on the C-arm mount 12. The distance of the radiation detector 16 relative to the radiation source 15 may be varied by displacing the radiation detector 16 along the central beam Z. The lifting device 27 has a driving motor 28, downstream of which a transmission 29 is arranged, by way of which a toothed wheel 30 is driven. The lifting device 27 may include the driving motor 28, the transmission 29 and the toothed wheel 30. The lifting device 27 may be rigidly arranged on the arm section 24. The toothed wheel 30 mates with a gear rack 31, which is arranged on the arm section 23. Guide rails 32 which are arranged opposite one another are embodied on the arm section 24 and/or its fastening section 25, on which guide rails 32 corresponding runner elements 33 of the moveable arm section 23 run. Depending on the actuation of the driving motor 28 by the control facility controlling the entire operation of the x-ray device 1, the movement of the toothed wheel 30 can be varied both in respect of the direction of rotation and also the rotational speed, so that the speed of travel and direction of movement of the arm section 23 supporting the radiation detector 16 can be varied. A position sensor system may be provided, which detects the exact positioning of the arm section 23 and thus of the radiation detector 16 relative to the radiation source 15. The lifting device 27 may be actuated as a function of such a position detection.

Even though a gear rack drive is shown, the integration of a spindle drive may be used. A driving spindle may be rotated by the driving motor, on which driving spindle one or several suitable spindle nuts, which would connect to the arm section 23, run. The arm section 23 may be linearly guided by linear guides (e.g. guide rails 32, runner elements 33). The interior of the arm may be subdivided into compartments with dividing walls instead of a framework support structure. For example, slide-in drawers, which are open from the side, may be used. The electronic components 21 may be integrated into these slide-in drawer compartments. In order to be able to pull communication or supply lines through the interior of the arm, there are local breaks in these dividing walls. An appropriate side cladding would naturally also be used.

In summary, a C-arm allows for significant weight savings, as a result of its open arm structure. The integration of the lifting device into the interior of the arm in the direct vicinity of the axis of rotation 17, about which the C-arm 14 can be rotated relative to the arm mount 12, which may optimize the center of gravity of the arm. The lifting device 27 is located in the immediate vicinity of the attachment of the C-arm to the robotic arm, the linear moving axis, along which the arm section 23 and thus the radiation detector 17 can be moved relative to the arm section 24 and/or the radiation source 15, is at right angles to the axis of rotation 17 in this arrangement. One further advantage of integrating the lifting device 27 into the interior of the arm in the region of the rotating connection to the robotic arm also consists in the C-arm no longer being designed as high as known x-ray devices on the detector side. This is because the lifting device usually arranged on the end of the arm in known x-ray devices requires considerable installation space, meaning that it extends away from the outside of the arm when viewed radially. This has occasionally been a restricting factor for an arm movement, in other words, many arm positions could not be adopted as a result of the arm protruding further out.

The invention claimed is:

1. An x-ray device comprising:
a radiation source and a radiation detector;
a robotic arm;
a C-arm that is rotatably mounted on the robotic arm, the radiation source and radiation detector being arranged on the C-arm; and
electronic components used to operate the radiation source and the radiation detector supported by the C-arm,
wherein an interior of the C-arm, which is hollow at least in sections, is accessible from at least one access side of the C-arm to allow integration of at least a portion of the electronic components into the interior of the C-arm, and
wherein the C-arm includes a first arm and a second arm, the first arm being separate from the second arm and being attached to and abutting the second arm to form a curved shape, the radiation source being arranged on one of the first arm and the second arm, and the radiation detector being arranged on the other of the first arm and the second arm.

2. The x-ray device as claimed in claim 1, wherein the C-arm is hollow and accessible from the at least one access side, the interior being accessible over an entire length of the C-arm.

3. The x-ray device as claimed in claim 2, wherein the interior of the C-arm is accessible from two access sides which are opposite to one another.

4. The x-ray device as claimed in claim 2, wherein the interior of the C-arm is subdivided into compartments by separating walls.

5. The x-ray device as claimed in claim 1, wherein the interior of the C-arm is accessible from two access sides which are opposite to one another.

6. The x-ray device as claimed in claim 5, wherein the two access sides are closed off by two detachable claddings.

7. The x-ray device as claimed in claim 5, wherein the interior of the C-arm is subdivided into compartments by separating walls.

8. The x-ray device as claimed in claim 1, wherein the C-arm has struts arranged to form a framework on the at least one access side.

9. The x-ray device as claimed in claim 1, wherein the interior of the C-arm is subdivided into compartments by separating walls.

10. The x-ray device as claimed in claim 1, wherein the at least one access side is closed off by a detachable cladding.

11. The x-ray device as claimed in claim 1, further comprising a lifting device arranged in the interior of the C-arm, wherein the first arm and the second arm are operable to be moved relative to one another by the lifting device arranged in the interior of the C-arm.

12. The x-ray device as claimed in claim 11, wherein the lifting device is a mechanical lifting device.

13. The x-ray device as claimed in claim 11, wherein the lifting device includes a spindle drive.

14. The x-ray device as claimed in claim 11, wherein the lifting device includes a hydraulic lifting device.

* * * * *